United States Patent [19]

Shamsuddin

[11] Patent Number: 5,162,202
[45] Date of Patent: Nov. 10, 1992

[54] RECTAL MUCUS TEST AND KIT FOR DETECTING CANCEROUS AND PRECANCEROUS CONDITIONS

[76] Inventor: Abulkalam M. Shamsuddin, 2916 Old Court Rd., Baltimore, Md. 21208-3311

[21] Appl. No.: 449,269

[22] Filed: Dec. 12, 1989

[51] Int. Cl.$^5$ ............ C12Q 1/26; C12Q 1/54; G01N 33/574
[52] U.S. Cl. .................. 435/25; 435/14; 435/7.23; 435/7.1; 436/501; 436/518; 436/808; 436/64; 436/813
[58] Field of Search ............ 435/967, 7.23, 7.1, 435/14, 25; 436/501, 518, 808

[56] References Cited

U.S. PATENT DOCUMENTS 4,857,457  8/1989  Shamasuddin et al. ............ 435/7

FOREIGN PATENT DOCUMENTS 0249418 12/1987 European Pat. Off. .

OTHER PUBLICATIONS

Kennedy et al., *Bioactive Carbohydrates*, John Wiley & Sons, N.Y., N.Y. 1983 pp. 70–72.
Fairbanks et al., "Electrophoretic Analysis of the Major Polypeptides of the Human Erythrocyte Membrane" Biochemistry vol. 10, No. 13 1971 pp. 2606–2617.
Dutt, M. K., Biological Abstracts, vol. 73, Abstract No. 69469 (1981).
Dutt; M. K., Biological Abstracts, vol. 72, Abstract No. 74604 (1981).
Dutt; M. K., Biological Abstracts, vol. 63, Abstract No. 16544 (1976).
Sakamoto et al., "A Pilot Study on the Usefulness of a New Test for Mass Screening of Colorectal Cancer in Japan," Gastroenterologia Japonica, vol. 25, No. 4, pp. 432–436 (1990).
McKenzie et al., "Expression of Carcinoembryonic Antigen, T-Antigen, and Oncogene Products as Markers of Neoplastic and Preneoplastic Colonic Mucosa," Human Pathology, vol. 18, No. 12, pp. 1282–1286 (Dec. 1987).

*Primary Examiner*—Esther L. Kepplinger
*Assistant Examiner*—Toni R. Scheiner
*Attorney, Agent, or Firm*—Millen, White, Zelano, and Branigan

[57] ABSTRACT

An improved rectal mucus screening test method and kit for cancerous and precancerous conditions which is rapid, employs reagents which can be provided in kit form and which does not give false negatives due to sampling error, immobilizes the mucus sample in a membrane filter, tests for marker carbohydrates which have vicinal galactose moieties and which are oxidized with galactose oxidase to vicinal aldehydic moieties which are visualized with Schiff's reagent and oxidizes those samples which test negative for the marker carbohydrates with periodic acid, renders the sample visualizable with Schiff's reagent, applies the galactose oxidase directly to the membrane filter, thereby speeding up color developed and employs the Schiff's Reagent which was refrigerated after preparation until the color faded to a straw shade before being treated with activated charcoal, which renders the solution storage stable ability for many months and enhances its color development ability.

2 Claims, No Drawings

RECTAL MUCUS TEST AND KIT FOR DETECTING CANCEROUS AND PRECANCEROUS CONDITIONS

BACKGROUND OF THE INVENTION

This invention relates to a screening test for cancerous and precancerous conditions of the large intestine and other body sites and to a kit containing the components necessary for conducting the test.

Cancer is a major public health problem in the world. Even as pharmaceutical agents for the treatment of cancer are developed, early detection and prevention are still the best hope for combating this human tragedy. Shamsuddin et al., *Human Pathology* 19:7–10, 1988, has recently developed a screening test for colorectal cancer which can detect cancer of the large intestine employing rectal mucus. The mucus is reacted with the enzyme galactose oxidase by moistening a cellulose membrane filter, which had previously been impregnated with a phosphate buffer solution of the enzyme and then lyophilized, and then contacting the moistened cellulose membrane filter with a Metricel membrane filter bearing the mucus sample for 1-2 hours. The mucus bearing membrane filter is then washed with distilled water for 1 minute, reacted with basic fuchsin for 15 minutes, washed in tap water for 10 minutes and then air dried. This procedure, although simple, is lengthy. It also suffers from the serious deficiency that, if a patient tests negative by the screening test, it can mean either a biological negative, i.e., the patient does not have a cancerous or precancerous condition which releases a marker carbohydrate employed in the screening test, or it is technically negative, i.e., and insufficient mucus from the rectum was obtained in order to detect any marker carbohydrate present therein. The latter situation could mean a "false negative", the consequence of which could be dangerous to the person tested since any cancer present could continue to grow undetected because the negative results would give the patient a false sense of security which might cause the patient or his/her physician to disregard symptoms that might otherwise be investigated if the negative results had not been obtained.

Another deficiency of the prior art test is the unstable nature of the basic fuchsin employed is a critical component therein. According to the prior art, basic fuchsin must be prepared fresh and discarded after a week because of its instability. (*Manual of Histological Staining Methods of the Armed Forces Institute of Pathology*, Ed. 3, McGraw-Hill, New York 1968, p. 159.) This makes it impossible to provide the materials required to conduct the screening test in kit form, since shipping, handling and storage of such kits would require a shelf life of at least six months and the instability of the basic fuchsin would preclude such a shelf life.

Finally, as noted above, the prior art screening test, in addition to several hours of preparation for lyophilization of galactose oxidase, requires more than two hours to obtain the results thereof, which makes the test impractical for mass screening of large segments of the population.

Since most cancers in humans are believed to be the result of exposure to one or more environmental carcinogens which are excreted through the large intestine or urinary bladder, it can be expected that the carcinogen(s) and/or their metabolite(s) cause changes in those organs. Based on this hypothesis or threat of the presence of a cancerous or precancerous condition in the body of an individual, including but not restricted to the large intestine, can be detected accurately by the method of this invention using rectal sampling, without the prior risk of false negatives which limited the value of this technique as a screening test for the general population. The present invention eliminates false negative results which are obtained as a result of inadequate sampling, permits rapid testing for the presence or absence of precancer or cancer carbohydrate markers in less than 15 minutes and ensures the stability of the critical components required to conduct the test for over one year.

OBJECTS OF THE INVENTION

It is a general object of the invention to provide a screening test for cancerous and precancerous conditions that does not suffer from the above-described deficiencies of the prior art test.

A more specific object of the present invention is to provide a novel screening test for cancerous and precancerous conditions which eliminates the error of technically false-negative results.

Another object of the invention is to provide such a test which can rapidly be performed, thereby facilitating its use in mass testing programs which do not require a special diagnostic laboratory.

Still another object of the invention is to provide a kit for conducting the screening test of this invention whose critical components are stable for a protracted period.

Still another object is to provide a method for performing the screening test employing the kit of this invention which can be completed fast enough to provide results for the tests to the individuals being tested while they wait.

Yet another object is to provide a method of preparing Schiff's Reagent, a component of the kit of this invention, which gives a much stronger color reaction and is storage-stable for many months, thereby rendering the kit commercially feasible for field testing.

Upon further study of the specification and appended claims, further objects and advantages of this invention will become apparent to those skilled in the art.

SUMMARY OF THE INVENTION

This invention relates to a method for field testing a plurality of human beings for cancerous and precancerous conditions which comprises the steps of (a) obtaining a sample of rectal mucus from each individual; (b) assaying each sample of rectal mucus for the presence therein of at least one of the marker carbohydrates beta-D-Gal-(1->3)-D-GalNAc, Fuc-alpha-1->2-Gal-beta-(1->4)-Fuc-alpha-1->3-GlcNAc, Fuc-alpha-1->2 Gal-beta-(1->4)-Fuc-alpha-1->3 GlcNAc-beta-(1->3)-Gal-beta-(1->4) GlcNAc and Fuc-alpha-1->2-Gal-beta-(1->4)-Fuc-alpha-1->3-GlcNAc-beta-(1->3)-Gal-beta-(1->4)-Fuc-alpha-1->3-GlcNAc; (c) and subjecting each sample which tests negative in the assay of step (b) to oxidizing conditions which are capable of oxidative ring opening of the cyclic sugar moieties of any glycoprotein present in the sample at a hydroxy group-bearing ring carbon atom thereof to form aldehydic sugar; and (d) then assaying the oxidized sample for the present of any aldehydic sugar moieties thus formed, the presence of thereby formed aldehydic sugar moieties confirming the adequacy of the mucus sampling, and the absence therein of thereby formed aldehyde sugar moieties establishing that the negative test results was due to mucus sampling error.

In a article of manufacture aspect, this invention relates to a diagnostic kit for detecting a cancerous or precancerous condition in human beings according to the test method of this invention which comprises galactose oxidase; a water-insoluble support capable of absorbing rectal mucus, a solution of basic fuchsin which is storage stable and periodic acid.

In a process aspect, this invention relates to a process for producing an aqueous solution of basic fuchsin suitable for use in the kit and method of this invention wherein a basic solution of fuchsin and a bisulfate is treated with activated charcoal and is stored at below room temperature before the activated charcoal is removed therefrom, the improvement which comprises storing the basic solution at below room temperature until the color thereof fades to a straw color before the activated charcoal is added thereto, thereby rendering the solution storage stable and enhancing the color development ability thereof.

DETAILED DISCLOSURE

Specific embodiments of the technique employed in this invention for detecting the presence of the marker carbohydrates in the rectal mucus of individuals tested for cancerous or precancerous conditions is disclosed in U.S. Pat. No. 4,857,457 and application Ser. No. 228,268, filed Aug. 4, 1988, of which I am one of the inventors. The assay method as disclosed in this patent, however, is slow, i.e., using the galactose oxidase strip test of Example 3 thereof requires several hours to obtain the results thereof. Moreover, there is no teaching therein of how one could confirm the adequacy of sampling when the test reaction is negative or how to conduct the test with Schiff's Reagent which is storage stable for many months, a fundamental requirement of a commercial kit containing a Schiff's Reagent.

The present invention is an improvement in the assay as described therein, with respect to eliminating technically false negative results, speed and with respect to the Schiff's Reagent which is employed therein, the latter feature making feasible the production of a kit which can be sold commercially for wide spread use because no reagent has to be made up prior to using the kit.

It was discovered, surprisingly, that if the generally accepted technique for producing the Schiff's Reagent of mixing the reagent after preparation with activated charcoal and then refrigerating is not followed, a solution which is storage stable for months at room temperature can easily and reproducibly be produced. This method renders the color reaction more intense than is obtained with conventional Schiff's Reagent. According to the technique of this invention, the Schiff's base is first refrigerated in the absence of activated charcoal, e.g., at about 0°-15° C., preferably about 0°-10° C., until the color thereof fades to a straw shade, e.g., for 1, 2 or more days, usually about 48 hours. After the solution has faded to a straw color, it is then treated with activated charcoal or like surface-active absorbent, e.g., with stirring, e.g., at room temperature for from about a few minutes to several hours or days. After removing the charcoal, e.g., by filtration, the Schiff's Reagent is filled into a vial or bottle of a volume suitable for conducting the number of tests for which the kit is designed, e.g., 1, 5, 10, 50, 100 or more.

The marker carbohydrates can be assayed employing an agglutination inhibition test, e.g., using an approximately stoichiometric amount of peanut agglutinin, by detecting the presence of biotinylated peanut agglutinin and detecting the complex by reacting it with avidin which is conjugated with one of the marker carbohydrates.

The marker carbohydrates can be detected by agglomeration of sensitized beads. The marker carbohydrates can also be detected by selective oxidation of the glycolprotein in the mucus sample with galactose oxidase or comparable oxidant which will oxidize the primary hydroxy groups of only the galactose moieties in the glycolprotein to aldehydic groups. If any of the galactose moieties are vicinal one to another, the resulting aldehydic groups will react with a Schiff's Reagent to form a magenta color.

The objects, features and advantages of the present invention are attained in one aspect thereof by providing a rapid, reliable with respect to false negatives and commercially feasible method for detecting the presence of a precancerous or cancerous condition in a human. The invention employs a test method which comprises obtaining a sample of rectal mucus, assaying the sample to detect the presence therein of at least one of the marker carbohydrates beta-D-Gal-(1->3)-D-GalNAc, Fuc-alpha-1->2-Gal-beta-(1->4)-Fuc-alpha-1->3-GlcNAc, Fuc-alpha-1->2 Gal-beta-(1->4)-Fuc-alpha-1->3 GlcNAc-beta-(1->3)-Gal-beta-(1->4)-GlcNAc or Fuc-alpha-1->2- Gal-beta-(1->4)-Fuc-alpha-1->3-GlcNAc-beta-(1->3)-Gal-beta-(1->4)-Fuc-alpha-1->3-GlcNAc; and, optionally, diagnosing the presence and degree of precancer or cancer based upon the amount of the marker carbohydrate(s) detected in the rectal mucus. Except for the modifications thereof of this invention which renders the test procedure rapid, reliable and commercially feasible, the test methods are those disclosed in U.S. Pat. No. 4,857,457 and prior filed application Ser. No. 228,268, filed Aug. 4, 1988, whose disclosures are incorporated herein by reference.

In one embodiment, the assay may be performed by reacting the body fluid with a precise amount of peanut agglutinin or other specific binding moiety for the disaccharide and then detecting the presence of unbound moiety. The reactant moiety can be immobilized onto a water-insoluble support, such as a membrane filter or solid beads of latex, plastic, glass, etc. In order to increase the sensitivity of the method, the reactant moiety can first be biotinylated in a conventional manner.

The complex can be detected by any of various suitable techniques, either directly or indirectly, e.g., immunologically, enzymatically, oxidative-reductively, etc. Presently preferred is the formation of a complex with avidin conjugated to a suitable marker, e.g., fuchsin or other dyes, radioactive labelling, fluorescent dyes such as fluorescein isothiocyanate or Rhodamine B, luminescent dyes such as luciferol, lumingl, biotin, etc.

The presence of the disaccharide beta-D-Gal-(1->3)GalNAc is readily detected by agglomeration of sensitized beads which have been coated with PNA, e.g., glass, agarose, polystyrene, latex, etc. A preferred method for detecting the presence of the complex is by selectively oxidizing the sugar moiety of the aforesaid disaccharide, e.g, with galactose oxidase, and detecting the presence of the oxidized sugar therein.

In a preferred embodiment of the invention, a kit is provided which comprises separate containers of galactose oxidase, a protein-capturing membrane filter, storage stable basic fuchsin, periodic acid and, optionally, deionized distilled water. Preferably the galactose oxidase is encapsulated or is impregnated into the same membrane filter onto which the mucus sample is applied. The pressure of smearing the mucus sample on the membrane filter is sufficient to activate the enzyme. The marker carbohydrate is then visualized by staining with basic fuchsin.

In one aspect, the assay test detects specific biochemical changes in rectal (large intestinal) mucus associated with a cancerous condition, e.g., of the large intestine, which results in the production of the disaccharide beta-D-Gal-(1->3)-D-GalNAc, also known as T-antigen, which is absent in the body fluids of normal individuals but is present in the rectal mucus of individuals with at least some cancerous and precancerous conditions. Shamsuddin et al. developed various techniques for the detection of this sugar moiety in a simple and inexpensive manner (but not as rapidly as the method employed in this invention or which permits the use of storage stable fuchsin or which eliminates false negatives), which techniques can be used to screen individuals for large intestinal diseases including cancer.

The lectin, peanut agglutinin (PNA) specifically binds with T-antigen and causes agglutination of T-antigen activated RBC. Exploiting these characteristics of PNA, initially a simple inhibition assay has been developed wherein T-antigen in a body fluid sample will bind with PNA and, therefore, PNA will not react with RBC and the red cells will accordingly not agglutinate. This test is very simple and can be performed rapidly. Using microtiter plates, a large number of samples can be screened in a short time. The galactose oxidase test can be done conveniently on a strip of membrane filter.

Because not all cancerous and precancerous conditions generate all of the marker carbohydrates identified herein in the same proportions, in a preferred embodiment more than one of the assay tests described herein is used to test the rectal mucus of an individual being screened for cancerous and precancerous conditions.

In addition to cancerous conditions, the tests used in methods of this invention has the power to detect other diseases of the colon including those that carry a high risk of cancer such as polyps, fistula, ureterosigmoidostomy, Crohn's disease, and ulcerative colitis.

Other properties, such as immobilization of PNA onto a water-insoluble support, immunological detection of the glycoconjugate or oxidation of the sugar moiety and detection by dyes, radio-chemicals, etc. can be exploited to develop additional assays. The use of an antibody directed against this sugar moiety in an immunoassay enables accurate estimation and monitoring of this moiety in rectal mucus as well as other body fluids. In the immunoassay the antibody can be tagged by a radioactive fluorescent or other suitable label for quantitative or semiquantitative detection.

Avidin, a glycoprotein (67,000 MW) has an extraordinarily high affinity for the vitamin biotin. Inasmuch as biotin molecules can be coupled to various proteins (biotinylation), avidin can be conjugated with various markers such as enzymes, dyes, heavy metals, radioactive isotopes, etc. Avidin has four binding sites for biotin, and many biotin molecules can be incorporated on a given protein. This amplification principle can be useful to detect minute amounts (i.e., ng/ml or even pg/ml) of the marker disaccharides in the glycoproteins of rectal mucus obtained during digital rectal examination.

Mucus glycoprotein containing the specific disaccharide will avidly bind to the lectins immobilized on a solid phase. A matrix formed by biotinylated lectins and enzyme-avidin D conjugate will bind to residual disaccharides on the immobilized glycoprotein lectins, while a suitable substrate will amplify the reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight. The entire disclosures of all applications, patents and publications, if any, cited above and below, and of corresponding application(s), are hereby incorporated by reference.

In all of the tests described herein, sterile gloves should be worn; forceps, scissors, and all work surfaces should be scrupulously clean membrane filters should be handled with forceps and filters must not be contaminated (even saliva may contaminate).

Hemagglutination Inhibition Test

This standard hemagglutination inhibition test, e.g., as described in U.S. Pat. No. 4,857,457, can be used in the marker carbohydrate test employed in this invention.

In typical results with this test, no false negatives and far fewer false positives (about one-third vs. about 95) are obtained than in the conventional fecal occult blood test. A negative test result is checked for proper mucus sampling procedure by testing the sample for glycoprotein content according to this invention.

Latex Agglutination Test

In this test, 500 $\mu$l of suspended latex beads (15.8$\mu$ diameter, Sigma Chemical Co., St. Louis, Mo.) are centrifuged at 3,000 RPM for 15 seconds and the supernatant is decanted. 500 $\mu$g of lectin, e.g., PNA, (Vector Laboratories Ltd., Burlingame, Calif.) is dissolved in 500 $\mu$l of carbonate buffer (pH 9.6) and added to the pellet of latex beads. The pellet is resuspended and incubated at 25° C. for 2 hours with occasional mild shaking to resuspend the beads and allow a more uniform binding. After incubation, the sample is centrifuged at 3,000 RPM for 15 seconds, the supernatant decanted, and the pellet resuspended in PBS (pH 7.4). Any unbound PNA is washed off by repeating the previous step three times. The final pellet is suspended and diluted 1:10 in PBS.

For testing a mucus sample collected during digital rectal examination, 10 $\mu$l of mucus in PBS is added to an equal amount of the latex beads and placed on a glass slide. After five minutes of incubation at 25° C., the slide is read. An agglutination of the beads, indicating the presence of the marker disaccharide is read as positive for a cancerous condition, whereas no agglutination after 5 minutes indicates either the absence of the disaccharide and hence a cancer-free status or sampling error. The latter possibility is eliminated in accordance with this invention by assaying the mucus sample for glycoprotein content.

Galactose Oxidase Strip Test

This technique uses the ability of galactose oxidase to selectively oxidize the C-6 hydroxyl group of galactose moieties of the glycoprotein in the mucus, e.g., both the galactose and N-acetyl galactosamine residues of the beta-D-Gal-(1->3)-D-GalNAc to D-galactohexodialdose. The presence of any vicinal aldehyde groups in this thus-oxidized product is evidence of a marker carbohydrate in the glycoprotein. Their presence can be detected using basic fuchsin reagent.

A mucus sample is obtained by digital examination of the rectum of a test individual with the gloved index finger. The mucus on the examining finger is smeared on the scored side of a piece of membrane filter, e.g., Metricel membrane filter 0.45 μm; Gelman Sciences, Inc., Ann Arbor, Mich. 48106). An appropriate amount (depending on the size of the filter paper) of galactose oxidase is applied directly to the filter. After 1 minute of reaction at room temperature, wash the membrane for 1 minute in deionized water and then place the membrane in Schiff's reagent for 1 minute and then wash the membrane for 1 minute in running tap water. Shake off excess water and dry the membrane by air drying or in an oven. A bright magenta coloration of the mucus smear when completely dried indicates a positive test.

With typical results, no false negatives and far fewer false positives (less than 10% vs. about 95%) are found than in the conventional fecal occult blood test. The samples giving a negative result are tested in accordance with this invention for glycoprotein content by oxidation with periodic acid followed by treatment again with Schiff's Reagent. Development of a magenta color confirms that the negative result is a biological negative and not a false negative due to sampling error.

Biotinylated Lectin Avidin-Enzyme Assay

Plant lectins, e.g., PNA dissolved in carbonate buffer (pH 9) to a final concentration of 100 ng/ml is used to coat the microtiter wells. 10 ng of lectins in 100 μl buffer are placed in each well and incubated at 37° C. for 2 hours. The wells are then washed off with phosphate buffered saline (PBS) pH 7.4, after which 100 μl of test mucus (dissolved in PBS) is added to the microtiter wells and the mixture is incubated at 37° C. for 1 hour. The wells are then washed three times with PBS to remove 100 μl of unbound mucus. Biotinylated lectins (1 μg/ml) is incubated for an additional hour at 37° C. in order to bind with residual marker carbohydrate (if any). The wells are washed three times with PBS to wash off unbound biotinylated lectins. Avidin-D-alkaline phosphatase (Vector Corporation, Burlingame, Calif.) is then added (100 μl/well, 1:50 dilution) to the wells and incubated for 1 hour at 37° C. Following 2 washes with PBS and 3 washes with bicarbonate buffer (pH 9.8), the substrate p-nitrophenyl phosphate (1 mg/ml) is added to the wells (100 μl/ well). Optical absorbance at 405 nm is read after 30 minutes incubation at 37° C. Mucus from known cancer patients give position results while mucus from non-cancer patients give negative results. In the event of a negative result, the adequacy of sampling is confirmed in accordance with this invention, e.g., with periodic acid followed by fuchsin.

Galactose Oxidase Strip Test Kit

The simple use test kit is packaged in a conventional manner in a cardboard carton containing (a) a capped vial containing an amount of storage stable basic fuchsin, prepared according to the Preparation hereinafter, sufficient to saturate twice (b) a strip of membrane filter, (Metricel membrane filter 0.46 μm, Gelman Sciences, Inc., Ann Arbor, Mich.). Also present in the kit is (c) an amount of a storage stable form of galactose oxidase which is present in the kit in a sealed capped bottle impregnated in the strip of membrane filter in an amount sufficient to oxidize marker carbohydrates in the sample. Also present are (d) periodic acid, and (e), a color chart for comparison with the test result and interpretation thereof.

For field testing purposes, the kit contains a plurality of the membrane filter strips, e.g., 5, 10, 50, 100 or more and the amounts of galactose oxidase, buffer solution and basic fuchsin solutions are increased proportionately.

PREPARATION

Storage Stable Schiff Reagent Solution

Dissolve 1.0 gm of basic fuchsin in 200.0 ml of hot distilled water and bring to the boiling point. Cool to 50° C., add 20.0 ml of 1N HCl and cool further and add 1.0 gm of sodium metabisulfate. Refrigerate in the dark until the solution becomes straw colored (about 48 hours). Then add 5 g of activated charcoal, thoroughly and remove the charcoal by filtration. The clear filtrate is a Schiff's Reagent which is storage stable for many months, e.g., at least one year. Moreover, the magenta color which is produced therewith is more intense than that obtained with conventionally prepared Schiff's Reagent.

EXAMPLES

Following the procedure described above for the galactose oxidase strip test, the rectal mucus of 382 individuals either with known cancerous or precancerous conditions of the large intestine or other body site or who were a symptomatic. The term "other body site" includes, but is not restricted to the uterine cervix, kidneys, head and neck, breast, lymphnode, blood, stomach, testes and prostate.

TABLE 1

| Large intestinal | | Other body site | High risk | |
|---|---|---|---|---|
| cancer | polyp | cancer | symptomatic | Normal |
| 31/34 | 53/85 | 10/16 | 95/190 | 3/57 |
| 91.2% | 63.5% | 62.5% | 50% | 5.2% |

The data in the first line are the number of individuals tested positive/total number of individuals in each category. Note that only 5% of the apparently normal (asymptomatic) individuals elicited a positive reaction.

In accordance with this invention, the mucus sample of each individual as evidenced by the absence of magenta coloration, was obtained by digital rectal examination with the gloved finger lubricated with either normal saline or other common lubricants used for such procedure. The mucus on the examining finger was smeared on the protein capturing membrane filter, reacted with galactose oxidase for 10 minutes at ambient temperature (25° C.), washed with deionized distilled water, reacted with basic fuchsin for 1 minute and then washed in tap water for 1 minute. The presence of a cancerous or precancerous condition is indicated by the magenta coloration of the mucus. Each sample which tests negative in this test as evidenced by the absence of magenta coloration, the sample was then reacted with periodic acid for 5 minutes, washed with deionized distilled water and reacted again with basic fuchsin for 1 minute and washed with tap water. The positive reaction eliciting a purple to magenta color is indicative of the fact that mucus glycoprotein had indeed been obtained but is negative with respect to the presence of the marker carbohydrate. The absence of magenta coloration means sampling error and the individual is tested again with a fresh mucus sample.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A diagnostic kit for detecting a cancerous condition in human beings and for determining sample sufficiency which comprises galactose oxidase; a water-insoluble support capable of absorbing rectal mucus; periodic acid; and a solution of basic fuchsin which is storage stable for at least one year and which is produced by storing a basic solution of fuchsin and sodium bisulfite at below room temperature until the color thereof fades to straw color and then treating the resulting solution with activated charcoal.

2. A diagnostic kit according to claim 1, wherein the basic fuchsin is a Schiff's Reagent and the water-insoluble support is a membrane filter.

* * * * *